United States Patent [19]
Lee et al.

[11] Patent Number: 5,877,385
[45] Date of Patent: Mar. 2, 1999

[54] PROCESS INCLUDING EXTRACTIVE DISTILLATION AND/OR DEHYDROGENATION TO PRODUCE STYRENE FROM PETROLEUM FEEDSTOCK INCLUDING ETHYL-BENZENE/XYLENE MIXTURES

[75] Inventors: Fu-Ming Lee, Katy; Stephen G. Norwood, Houston; Joseph C. Gentry, Houston, all of Tex.

[73] Assignee: HFM International, Inc., Houston, Tex.

[21] Appl. No.: 719,692

[22] Filed: Sep. 26, 1996

Related U.S. Application Data

[63] Continuation-in-part of Ser. No. 651,707, May 21, 1996, abandoned.

[51] Int. Cl.[6] .............................. C07C 7/08; C07C 7/10
[52] U.S. Cl. ................... 585/807; 585/441; 585/806; 585/808; 585/819; 585/833; 585/857; 585/862; 585/860; 585/863; 585/868; 585/864; 585/866; 585/435; 585/440
[58] Field of Search ............................ 585/440, 441, 585/806, 807, 808, 819, 833, 857, 862, 860, 863, 868, 864, 866, 435

[56] References Cited

U.S. PATENT DOCUMENTS

| | | | |
|---|---|---|---|
| 2,380,019 | 7/1945 | Bloomer | 202/42 |
| 2,385,235 | 9/1945 | Schneider | 202/42 |
| 2,467,197 | 4/1949 | Engel | 202/42 |
| 2,831,039 | 4/1958 | Nevitt | 260/674 |
| 3,018,228 | 1/1962 | Cornell | 202/39.5 |
| 3,684,665 | 8/1972 | Abe et al. | 203/9 |
| 3,763,015 | 10/1973 | Morimoto et al. | 203/9 |
| 3,953,300 | 4/1976 | Ginnasi et al. | 203/53 |
| 5,196,632 | 3/1993 | Larsen et al. | 585/440 |

OTHER PUBLICATIONS

SRI Report #33, section 8, pp. 109–128, "Recovery Styrene from Pyrolysis Gasoline", Mar. 1973.
Handbook of Chemistry and Physics; David R. Lide; 75th edition, 1995.

*Primary Examiner*—Glenn A. Caldarola
*Assistant Examiner*—Thuan D. Dang
*Attorney, Agent, or Firm*—Jenkens & Gilchrist, P.C.

[57] ABSTRACT

Disclosed is a process for recovering styrene from a feedstock containing at least styrene, ethylbenzene, and one or more aromatic or non-aromatic hydrocarbon compounds which includes separating said feedstock into a first stream relatively more concentrated in styrene than said feedstock and a second stream relatively more concentrated in ethylbenzene than said feedstock, recovering styrene from said first stream to produce a styrene product stream, dehydrogenating the ethylbenzene of said second stream to produce additional styrene, and recovering said additional styrene. The feedstock may be separated into said first and second streams by a process selected from the class consisting of extractive distillation, azeotropic distillation, distillation, liquid-liquid extraction, chemical complex formation, membrane separation, and combinations thereof, and the additional styrene may be recovered by recycling it into said feedstock.

20 Claims, 5 Drawing Sheets

PROCESS INCLUDING EXTRACTIVE DISTILLATION AND/OR DEHYDROGENATION TO PRODUCE STYRENE FROM PETROLEUM FEEDSTOCK INCLUDING ETHYL-BENZENE/XYLENE MIXTURES

RELATED APPLICATION

This application is a continuation-in-part of a United States patent application entitled "Recovery of Styrene From Pyrolysis Gasoline by Extractive Distillation," Ser. No. 08/651,707, filed May 21, 1996, now abandoned as the invention of Fu-Ming Lee, Joseph C. Gentry and Randi Wright Wytcherley, and assigned to the assignee of the present application. The disclosure of application Ser. No. 08/651,707 is incorporated herein by reference.

This invention relates to the art of producing and/or recovering styrene from various hydrocarbon feedstocks, principally petroleum feedstocks, when the term "feedstock" is understood to include various intermediate streams created during the processing of crude oil or liquid natural gas (LNG) or other mixed hydrocarbons to produce refined petroleum products. Such feedstocks may include those having a styrene content, such as pyrolysis gasoline, as well as those initially containing little or no styrene, but containing a related material, ethylbenzene. An example of such a feedstock is a $C_8$ reformate fraction.

BACKGROUND OF THE INVENTION

In the course of refining petroleum to produce fuel, lubricant, and petrochemical starting material products, there are various streams of intermediates created. Some of these streams are high in $C_8$'s, and contain in particular some styrene and/or some ethylbenzene, which is a material related to styrene in that hydrogenation of styrene will produce ethylbenzene, and dehydrogenation of ethylbenzene will produce styrene. Because of its tendency to dimerize and polymerize, styrene is considered to be a troublesome component of gasoline stock intended ultimately for fuel use. Furthermore, use of styrene in fuel is not as high an economic use for the product as other petrochemical uses, such as a starting material for making polystyrene. In addition, there is a growing demand for polystyrene type products, and hence a growing demand for styrene as a starting material or precursor of such products.

In the above-mentioned parent application from which the present application is a continuation-in-part, there are disclosed techniques for separating styrene from other materials commonly found in pyrolysis gasoline, especially mixed xylenes and ethylbenzene.

SUMMARY OF THE INVENTION

The present invention makes use of the techniques disclosed in the parent application, particularly the extractive distillation techniques, together with careful selection, arrangement and combination of pre-processing and post-processing steps in connection with these extractive distillation techniques to separate and recover not only the styrene which may be found in the intermediate streams of the refining process, but also ethylbenzene, which may be found in or produced in such streams and including, when desired, conversion of the ethylbenzene to yield additional styrene. The pre-processing and post-processing steps include those such as hydrogenation, dehydrogenation, splitting prior to or after the extractive distillation steps, as well as splitting during extractive distillation steps. These combinations, in accordance with the invention, make possible more complete recovery of styrene actually and potentially present in such intermediate streams with great flexibility and efficiency and simplicity of equipment arrangements.

In accordance with the invention considered broadly, a process is provided for recovering styrene from a feedstock containing at least styrene, ethylbenzene, and one or more aromatic or non-aromatic hydrocarbon compounds. The process includes separating the feedstock into a first stream relatively more concentrated in styrene than the feedstock and a second stream relatively more concentrated in ethylbenzene than the feedstock, recovering styrene from said first stream to produce a styrene product stream, dehydrogenating the ethylbenzene of said second stream to produce additional styrene, and recovering said additional styrene. The feedstock is separated into said first and second streams by a process selected from the class consisting of extractive distillation, azeotropic distillation, distillation, liquid-liquid extraction, chemical complex formation, membrane separation, and combinations thereof. Preferably, the additional styrene is recovered by recycling it into said feedstock.

In accordance with the invention, a process is provided for producing styrene from a feedstock containing styrene and at least one aromatic or non-aromatic hydrocarbon which includes feeding said feedstock into a distillation zone; feeding a two-part extractive solvent into said distillation zone, said solvent consisting essentially of a first part selected from the group consisting of propylene carbonate, sulfolane (tetramethylene sulfone), methyl carbitol, 1-methyl-2-pyrrolidinone, 2-pyrrolidinone and mixtures thereof and a second part consisting of water; distilling said feedstock in said distillation zone in the presence of said extractive solvent to produce: (a) a solvent fraction relatively rich in styrene compared to the solvent fed to said distillation zone; and (b) an overhead fraction comprising at least some of said at least one close boiling aromatic or non-aromatic hydrocarbon and being relatively lean in styrene compared to said feedstock; withdrawing said solvent fraction from said distillation zone; withdrawing said overhead fraction from said distillation zone; and separating at least styrene and ethylbenzene from one another in the course of performing the foregoing steps of said process.

In a preferred form of the process just outlined, the further step of hydrogenating at least part of said feedstock prior to feeding said feedstock to said distillation zone to hydrogenate any acetylenic compounds therein under conditions avoiding conversion of substantial amounts of styrene to ethylbenzene is included. Another preference for some applications is that separation of styrene and ethylbenzene is effected in said distillation zone. Similarly, it is also preferred for some operations that the ethylbenzene following its separation from styrene is dehydrogenated to produce additional styrene, and furthermore, the additional styrene may be returned to said distillation zone as a recycle stream.

When, in accordance with a preferred form of the invention mentioned above, separation of styrene and ethylbenzene is effected in the distillation zone, the withdrawn solvent fraction containing styrene and at least some of said aromatic or non-aromatic hydrocarbon may preferably be fed to a second distillation zone in some applications and additional extractive solvent may be fed to said second distillation zone, and distillation of said styrene and said at least some of the one aromatic or non-aromatic hydrocarbon be carried out in the presence of said extractive solvent to effect a further separation of styrene from the one aromatic or non-aromatic hydrocarbon, following which said further separated styrene from said second distillation zone is withdrawn. Moreover, said further separated styrene which is admixed with solvent when withdrawn from said second distillation zone may then be separated from said admixed solvent.

In another preferred variation of the process hereinabove outlined, separated ethylbenzene is further partly or totally separated from any other $C_8$ materials present with it prior to the above referred to dehydrogenation step. Also, separated styrene which is admixed with solvent when withdrawn from said distillation zone may be separated from said admixed solvent.

A still further variation of the above described process of the invention is one in which said feedstock, after said hydrogenation of at least part thereof, is separated to produce an overhead feedstock stream containing at least some ethylbenzene, some p-xylene, and some m-xylene, and a bottoms stream containing o-, p-, and m-xylenes with no or only a minor amount of ethylbenzene, following which said overhead feedstock stream is dehydrogenated to produce some styrene therein, following which $C_7$'s and lighter components, if any, are separated therefrom prior to said hydrogenated feedstock being fed into said distillation zone.

Another preferred form of the process is one in which any non-aromatic components present in said hydrogenated feedstock are separated from said styrene in said distillation zone. It should further be noted that the solvent fraction relatively rich in styrene may be fed to a second distillation zone, and additional extractive solvent may also be fed to said second distillation zone to facilitate distilling said styrene, said ethylbenzene and any other aromatic $C_8$ hydrocarbons present in said solvent fraction in the presence of said extractive solvent to effect a further separation of styrene from said ethylbenzene and said any other aromatic $C_8$ hydrocarbons, following which said separated styrene may be withdrawn from said second distillation zone.

In accordance with the invention, there is provided a process for recovering styrene from a feedstock containing at least styrene, ethylbenzene, o-xylene, m-xylene and p-xylene which includes hydrogenating said feedstock to selectively hydrogenate any acetylenic compounds therein while avoiding conversion of substantial amounts of styrene to ethylbenzene; feeding said hydrogenated feedstock into first distillation zone; feeding a two-part extractive solvent into said first distillation zone, said solvent consisting essentially of a first part selected from the group consisting of propylene carbonate, sulfolane (tetramethylene sulfone), methyl carbitol, 1-methyl-2-pyrrolidinone and mixture thereof and a second part consisting of water; distilling said feedstock in said first distillation zone in the presence of said extractive solvent to produce: (a) a first solvent fraction containing styrene, o-xylene, m-xylene, p-xylene and said extractive solvent; and (b) a first overhead fraction containing ethylbenzene, some p-xylene and m-xylene and any non-aromatic hydrocarbons; dehydrogenating said first overhead fraction to produce additional styrene; feeding said dehydrogenated first overhead fraction to a second distillation zone and distilling it there to produce: (c) a second overhead fraction containing primarily $C_7$ and lighter hydrocarbon materials; and (d) a bottoms stream containing styrene, ethylbenzene, p-xylene and m-xylene; withdrawing said second overhead fraction; recycling said bottoms stream to said selective hydrogenation step; feeding said first solvent fraction to a third distillation zone; feeding said two-part extractive solvent into said third distillation zone; distilling said first solvent fraction in said third distillation zone in the presence of said extractive solvent to produce: (e) a second solvent fraction containing said solvent and styrene; and (f) a third overhead fraction containing mixed xylenes; stripping and withdrawing styrene from said extractive solvent in said second solvent fraction; and recycling said stripped extractive solvent to said first and third distillation zones for use therein.

Another preferred form of the invention is a process for recovering styrene from a feedstock containing at least styrene, ethylbenzene, o-xylene and p-xylene including hydrogenating said feedstock to hydrogenate any acetylenic compounds therein while avoiding conversion of substantial amounts of styrene to ethylbenzene; feeding said hydrogenated feedstock into a first distillation zone; feeding a two-part extractive solvent into said first distillation zone, said solvent consisting essentially of a first part select from the group consisting of propylene carbonates, sulfolane, methyl carbitol, 1-methyl-2-pyrrolidone, 2-pyrrolidinone, and mixtures thereof, and a second part consisting of water; distilling said feedstock in said first distillation zone in the presence of said extractive solvent to produce: (a) a first solvent fraction containing styrene and said extractive solvent; and (b) a first overhead fraction containing ethylbenzene, o-xylene, m-xylene, and p-xylene; feeding said first overhead fraction to a second distillation zone and distilling it thereto produce: (c) a bottoms fraction containing mixed xylene; and (d) a second overhead fraction containing ethylbenzene, p-xylene, and m-xylene; dehydrogenating said second overhead fraction to produce additional styrene; feeding said dehydrogenated second overhead fraction to a third distillation zone and distilling it there to produce: (e) a third overhead fraction containing $C_7$ and lighter hydrocarbon materials; and (f) a second bottoms fraction containing styrene, ethylbenzene, p-xylene and m-xylene; withdrawing said third overhead fraction; recycling said second bottoms fraction into said feedstock; stripping and withdrawing styrene from extractive solvent in said first solvent fraction; and recycling said stripped extractive solvent to said first distillation zone for use therein.

Yet another preferred embodiment of the invention involves a process for producing styrene from a $C_8$ reformate fraction feedstock containing ethylbenzene, o-xylene, m-xylene and p-xylene including splitting said $C_8$ reformate fraction feedstock in a first distillation column to produce first overhead stream containing ethylbenzene and a portion of the m-xylene and p-xylene in said feedstock and a first bottom stream containing o-xylene, m-xylene and p-xylene; dehydrogenating said first overhead stream to convert part of the ethylbenzene therein to styrene; splitting said dehydrogenated first overhead stream in a second distillation zone to produce a second overhead stream containing $C_8$ and lighter hydrocarbons and a second bottom stream containing styrene, ethylbenzene, p-xylene and m-xylene; feeding said second bottom stream into a third distillation zone; feeding a two-part extractive distillation solvent into said third distillation zone, said solvent consisting essentially of a first part selected from the group consisting of propylene carbonate, sulfolane (tetramethylene sulfone), methyl carbitol, 1-methyl-2-pyrrolidinone, 2-pyrrolidinone and mixtures thereof and a second part consisting of water; distilling said second bottom stream in said distillation zone in the presence of said extractive distillation solvent to produce: (a) a solvent fraction containing styrene and solvent; and (b) a third overhead stream containing ethylbenzene, p-xylene, and m-xylene; recycling said third overhead stream to said $C_8$ reformate fraction feedstock;

stripping and removing styrene from solvent in said solvent fraction; and recycling said stripped solvent to said third distillation zone.

Still another process according to the invention is one for recovering styrene from a feedstock containing at least styrene, ethylbenzene, o-xylene, m-xylene and p-xylene comprising hydrogenating said feedstock to hydrogenate any acetylenic compounds therein while avoiding conversion of substantial amounts of styrene to ethylbenzene; feeding said hydrogenated feedstock into a first distillation zone; feeding a two-part extractive solvent into said first distillation zone, said solvent consisting essentially of a first part selected from the group consisting of propylene carbonate, sulfolane (tetramethylene sulfone), methyl carbitol, 1-methyl-2-pyrrolidinone and 2-pyrrolidinone, and mixtures thereof, and a second part consisting of water; distilling said feedstock in said first distillation zone in the presence of said extractive solvent to produce: (a) a first solvent fraction containing styrene, o-xylene, m-xylene, p-xylene and said extractive solvent; and (b) a first overhead fraction containing $C_8$ non-aromatics; feeding said first solvent fraction to a second distillation zone; feeding said two-part extractive distillation solvent into said second distillation zone; distilling said first solvent fraction in said second distillation zone in the presence of said extractive solvent to produce: (c) a second solvent fraction containing said solvent and styrene; and (d) a second overhead fraction containing $C_8$ aromatics; stripping and withdrawing styrene from said extractive solvent in said second solvent fraction; and recycling said stripped extractive solvent to said first and second distillation zones for use therein.

The foregoing aspects and features and embodiments of the present invention may be better understood by considering the detailed description which follows, together with the accompanying drawings.

DESCRIPTION OF THE PREFERRED EMBODIMENTS

Figure 1:
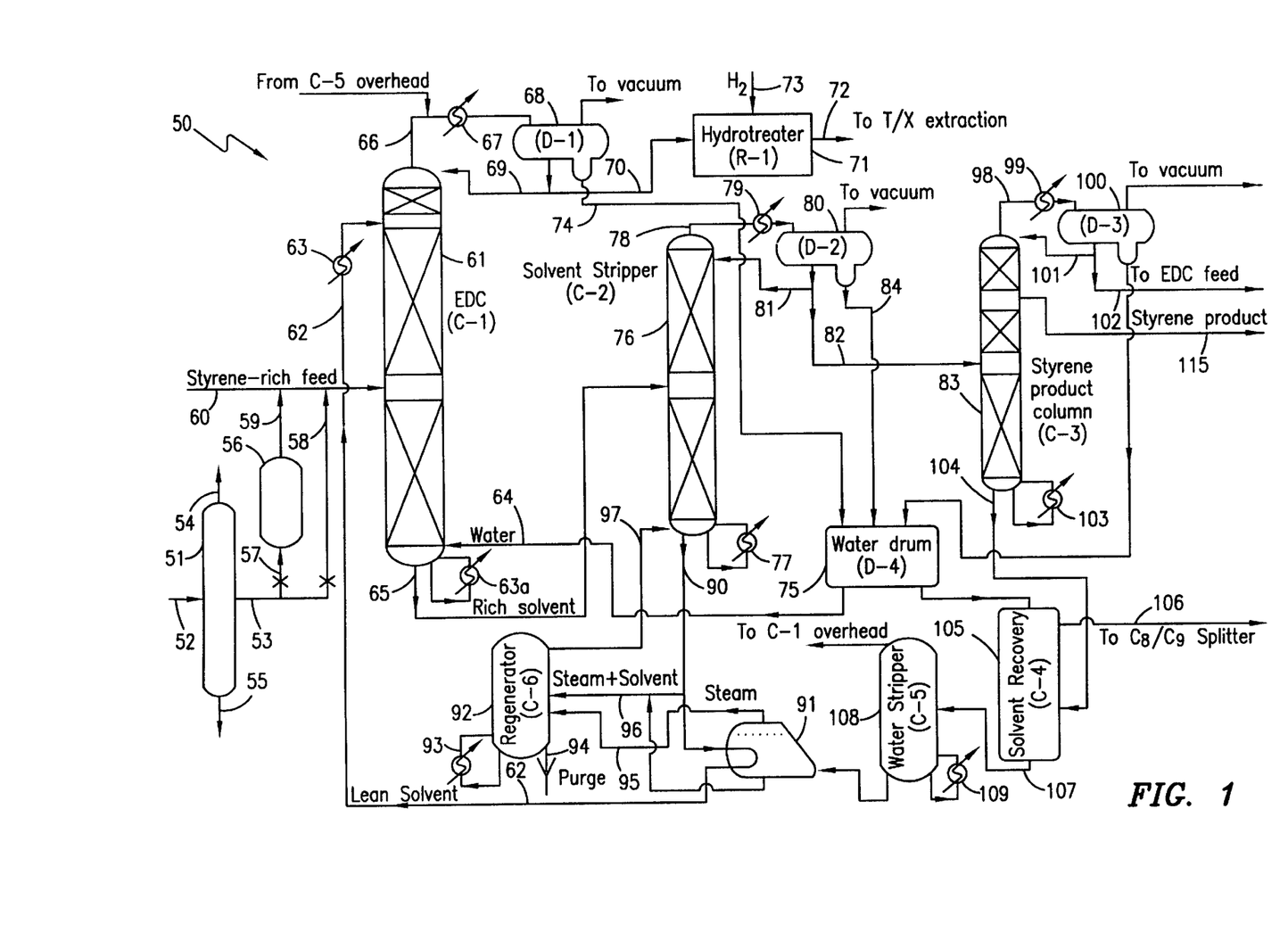
FIG. 1 is a diagrammatic illustration in elevation of an industrial plant for practicing certain aspects of the present invention, and is substantially the same as FIG. 4 of the above-identified parent application.

FIG. 1 is a diagrammatic illustration in elevation of an industrial plant for practicing the present invention and is substantially the same as FIG. 4 of the above-identified parent application. A preferred, but optional, element of the plant 50 is a fractionator 51, which is fed pyrolysis gasoline through line 52, and which effects a tight separation of $C_8$'s, which leave the tower through line 53, with $C_7$ and lighter materials leaving the fractionator 51 through line 54, and $C_9$ and heavier materials leaving the tower as bottoms through line 55. This operation may be accomplished in one or more sequentially arranged fractionation columns.

Preferably, but also optionally, the closely fractionated $C_8$ stream is fed through a hydrogenator 56 through line 57. The hydrogenation process carried out therein is mild enough to selectively hydrogenate any acetylenic compounds, such as phenylacetylene, without converting an objectionable proportion of the styrene to ethylbenzene. Since this step is optional, a bypass line 58 and appropriate valving are shown for omitting it. The output of the hydrogenator is fed through line 59, together with styrene-rich feed obtained through line 58, or from any other source through line 60, into the extractive distillation column 61. Column 61 is shown as a packed tower, although any suitable type of mass transfer device may be used. Lean solvent is introduced to the tower through line 62 from portions of the plant to be discussed below. It is fed at a point above the feed of the styrene-rich material through line 60. Heat is applied to the tower by heater 63 in the lean solvent input line, and by reboiler circuit 63a at the bottom of the column. In accordance with the invention, water as a second component of the extractive distillation solvent is introduced into the extractive distillation column 61 through line 64.

In the extractive distillation column 61, the distillation conditions are so modified by the lean solvent and the water component that the styrene tends to flow downwardly through the tower to exit with the rich solvent through bottom line 65, while the other aromatics and the non-aromatics are distilled overhead through line 66. The aromatics in this stream are primarily $C_8$'s, i.e., ethylbenzene and meta-, ortho- and para-xylene, and the non-aromatic overhead material is primarily $C_9$ napthenes and $C_9$ paraffins. The overhead stream in line 66 is passed through condenser 67 to separator drum 68 where a portion of it is withdrawn and fed back as reflux through line 69. The balance of the organic part of the overhead condensate is fed through line 70 through hydro treater 71, where it is hydrogenated to produce a mixture which is primarily toluene/xylene that is fed through line 72 to a toluene/xylene extraction unit (not shown). Hydrogen for the hydro treater is supplied through line 73. Water is drawn from the condensate drum 68 from a deep leg thereof through line 74, which feeds it to water drum 75.

The styrene-rich solvent from the bottom line 65 of the extractive distillation column 61 is fed to solvent stripper 76, which is also shown as a packed tower, although any suitable type of mass transfer device may be used. Heat for stripping is supplied to the tower in part by reboiler circuit 77. In the solvent stripper 76, the separation of styrene from the solvent is effected, and the styrene leaves the stripper through overhead line 78. It is passed through condenser 79 into condensate drum 80. A portion of the condensate is withdrawn and fed through line 81 as reflux to the top of the stripper tower 76. The balance of the hydrocarbon stream is fed through line 82 to the styrene purification column 83. Water is withdrawn from a deep leg of the condensate drum 80 through line 84, which delivers it to water drum 75.

The bottom stream from solvent stripper 76 is lean solvent, which leaves the tower through line 90 and is passed through a steam generator 91 and lean solvent cooler 63 for removal of heat before being fed back to the extractive distillation column 61 through line 62. A solvent regenerator 92 is provided with a reboiler circuit 93 and a purge line 94. It receives some lean solvent through side draw line 96 from lean solvent line 90 and from steam generator 91 through line 95. The output of the regenerator 92 is fed back into the bottoms of the solvent stripper through line 97.

In the styrene purification column 83, which is also drawn as a packed tower, although any suitable type of mass transfer device may be used, the components of the stripped and highly purified styrene stream are fed to the tower through line 82; those which are lighter than styrene are taken overhead through line 98 and passed through condenser 99, and are delivered to condensate drum 100. One material so removed is cyclopentadiene (CPD), the monomer of dicyclopentadiene (DCPD). This monomer tends to dimerize to DCPD, which in turn tends to crack back to CPD. Both CPD and DCPD are deleterious if left in the styrene product stream. The lighter overhead stream is drawn from condensate drum 100; a portion of it is fed back as reflux through line 101 and the remainder is fed through line 102 to be fed back into the extractive distillation column 61. A reboiler circuit 103 is provided at the bottom of column 83 to supply heat for operating the column. The bottom stream from purification column 83 is withdrawn through line 104 and includes residual traces of high boiling aromatic hydrocarbons, traces of polystyrene, and small amounts of other hydrocarbons, and traces of solvent. These are processed in a solvent recovery column 105; the top stream out of the solvent recovery column is delivered to a $C_8 / C_9$ splitter, such as 51, through line 106, and the bottom stream is fed through line 107 to a water stripper 108. Water from water drum 75 is fed in part back to the base of the extractive distillation column 61, and in part to the top of the solvent recovery column 105. A water stripper column 108 is provided with a reboiler circuit 109. The overhead from the water stripper is fed back to join the overhead stream in line 66 out of the top of the extractive distillation column 61, while the bottom stream out of the water stripper is fed into boiler 91.

Purified styrene is separated into a styrene purifier side stream and withdrawn through line 115.

All of the fractionating columns are preferably operated under vacuum in order to lower the boiling points of the materials involved.

Figure 2:
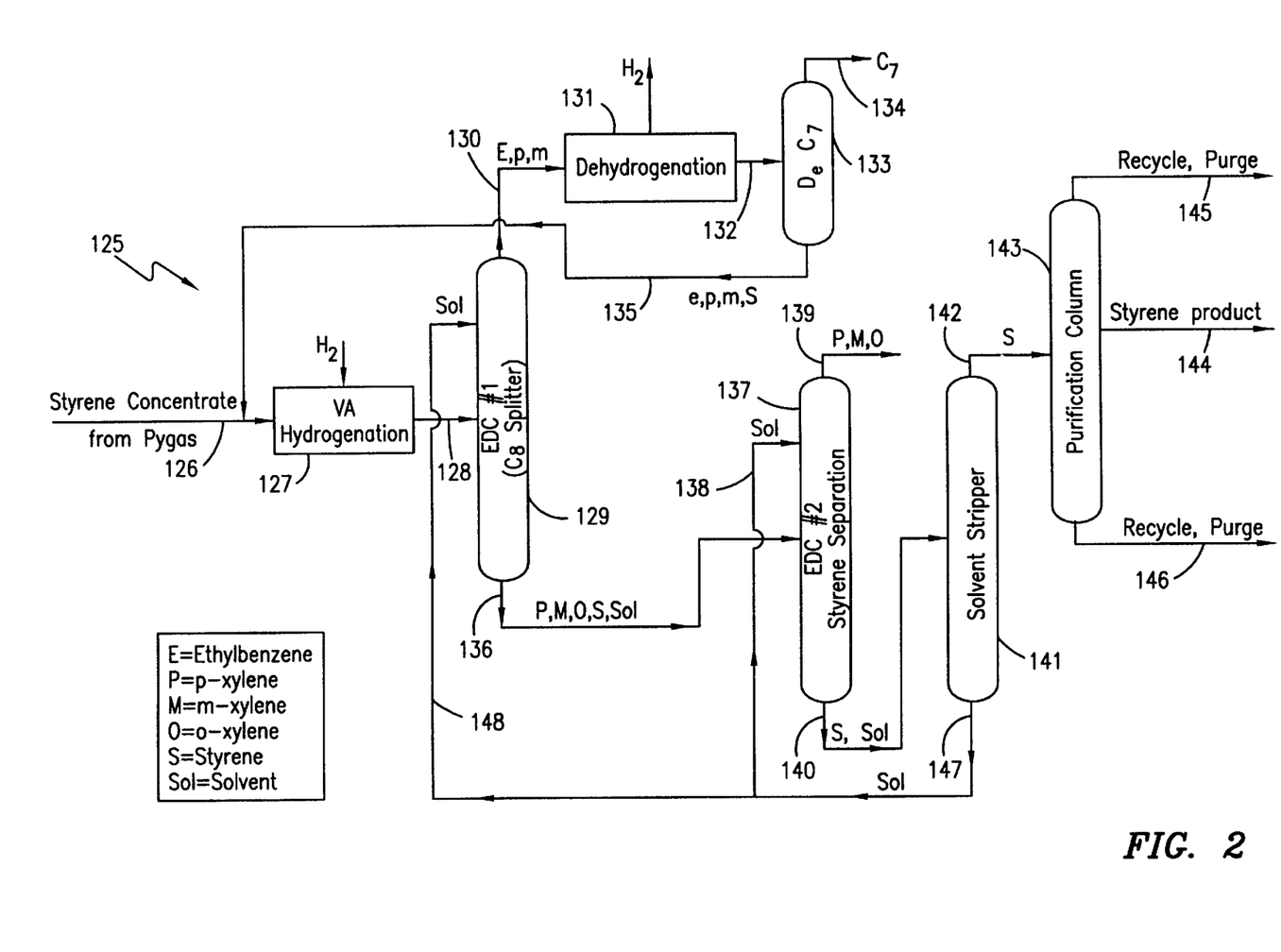
FIG. 2 is a diagrammatic illustration in elevation of an industrial plant for practicing a preferred embodiment of the invention involving particularly splitting of the $C_8$'s in the feedstock.

In the embodiment shown in FIG. 2, pyrolysis gasoline feedstock is fed to the plant 125 through input line 126. The incoming feedstock is a pyrolysis gasoline having a relatively high styrene content. It is first hydrogenated in vinyl acetylene hydrogenator 127 under relatively mild conditions to hydrogenate any acetylenic compounds present without converting a substantial amount of the styrene to ethylbenzene. The hydrogenated feedstock is then fed through line 128 into column 129, which is an extractive distillation column operated under conditions such that it is also a splitter of $C_8$ materials. The operating conditions in the extractive distillation column 129 are such that the overhead stream leaving through line 130 is relatively rich in ethylbenzene and contains some p-xylene and m-xylene. The bottom stream from extractive distillation column 129 is relatively concentrated in p-xylene, m-xylene, o-xylene, styrene, and extractive distillation solvent. The preferred solvent, as is discussed in the parent of this application is sulfolane and water.

The ethylbenzene rich overhead stream leaving column 129 through line 130 is dehydrogenated in the hydrogenator 131 to convert ethylbenzene to styrene. The dehydrogenated stream is passed through line 132 to a splitter column 133 where it is split into an overhead stream leaving through line 134, and comprising mainly $C_7$'s and lighter hydrocarbon materials, and a bottom stream leaving column 133 through line 135 containing mixed xylenes and styrene. The bottom stream leaving through line 135 is preferably recycled and joined with the incoming feedstock through line 126. The bottom stream 135 also contains some unreacted ethylbenzene.

From the portion of the embodiment of FIG. 2 discussed thus far, it can be seen that one of its features is a splitting of the ethylbenzene material out of the feedstock early in the process. Another feature is accomplishing this $C_8$ splitting operation in an extractive distillation column. Still further, a feature of this embodiment is the dehydrogenation of the largely ethylbenzene overhead stream to produce additional styrene product which is eventually recovered by being recycled back through the extractive distillation column.

The bottom stream from the extractive distillation column 129, leaving through line 136, contains substantial proportions of p-, m-, and o-xylenes, as well as styrene and extractive distillation solvent. This bottom stream is fed into second extractive distillation column 137, together with additional extractive distillation solvent through line 138. In extractive distillation column 137, further separation of the species is accomplished, and through overhead line 139, an overhead stream consisting mainly of mixed xylenes, constituting a product of value for further processing, is recovered. Out of the bottom of extractive distillation column 137 is recovered styrene and solvent through line 140.

The bottom stream passing through line 140 is fed into a stripper column 141 which separates the styrene from the solvent. The styrene leaves as an overhead stream through line 142 and is fed to a purification column 143. In this column, the styrene is separated from both lighter and heavier impurity streams and is taken off as a purified styrene product through side stream 144. The overhead stream through line 145 and bottom stream through line 146 may be recycled or discarded.

The recovered and separated solvent leaves solvent stripper 141 through bottom line 147. A portion of the recovered solvent is fed through line 148 to the first extractive distillation column 129 and the remaining recovered solvent is fed through line 138 to the second extractive distillation column 137.

It should be noted that performing the $C_8$ splitting in an extractive distillation operation enhances the efficiency of the separation in this particular embodiment. It should also be noted that incoming ethylbenzene is essentially recycled to extinction through the dehydrogenation loop and converted into valuble styrene. The increase in styrene recovery may be as much as 30% or more. Another advantage of this arrangement is that the load on the second extractive distillation column is reduced because there is little or no ethylbenzene or non-aromatics in the feed to that column. A further advantage is that a high quality mixed xylenes product stream is created in the arrangement of FIG. 2.

Figure 3:
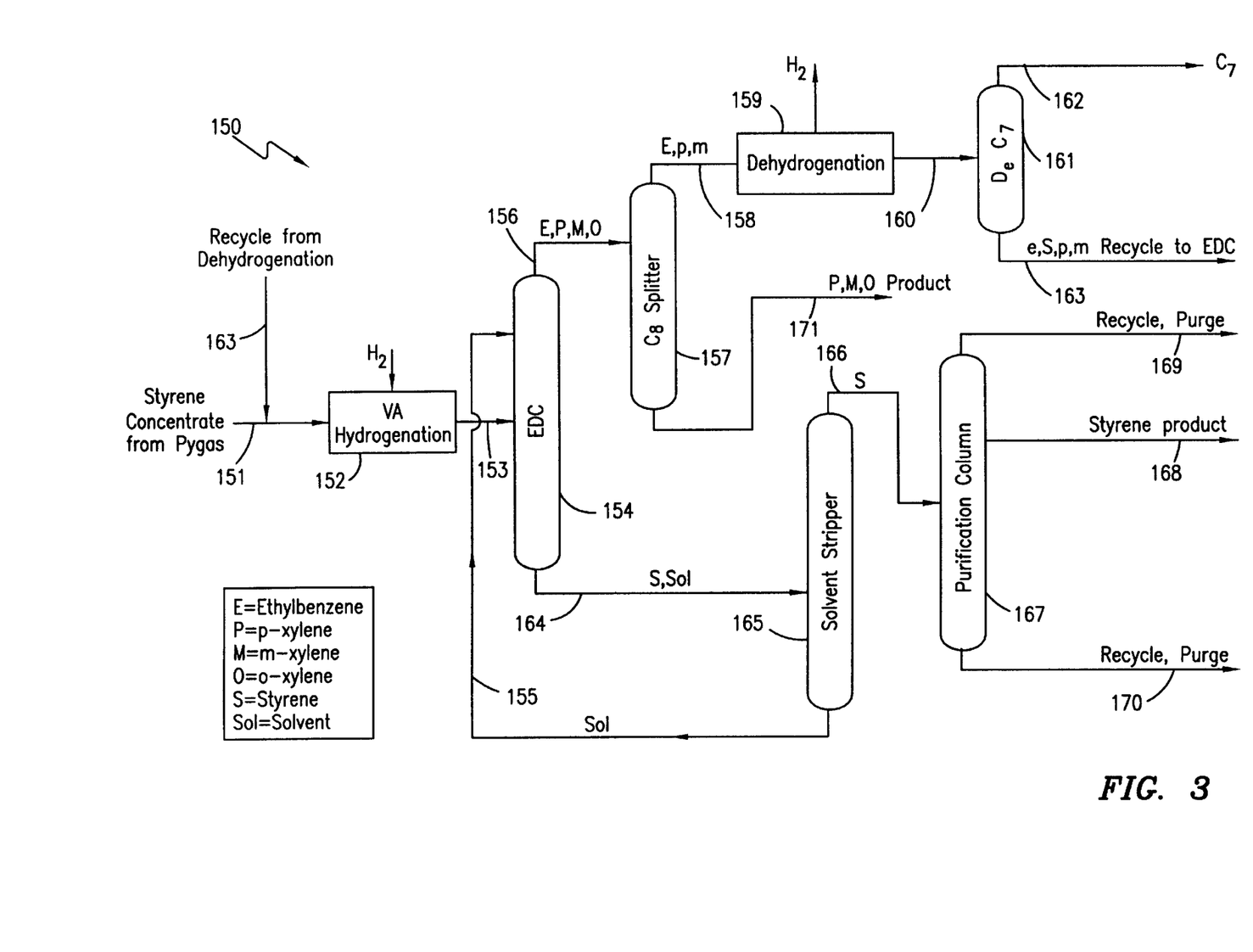
FIG. 3 is a diagrammatic illustration in elevation of an industrial plant for practicing another preferred form of the invention involving particularly $C_8$ raffinate splitting as part of the process.

In the embodiment shown in FIG. 3, the plant 150 receives feedstock containing styrene through line 151. Similarly to other embodiments, it is mildly hydrogenated in hydrogenator 152 to eliminate any acetylenic compounds without unduly converting styrene to ethylbenzene. The hydrogenated feedstock is fed through line 153 into an extractive distillation column 154 where it is extractively distilled in the presence of a solvent such as sulfolane and water which is fed in through line 155. The overhead line 156 from extractive distillation column 154 carries off a raffinate stream containing substantial portions of ethylbenzene and mixed xylenes. These are fed to a distillation column arranged to operate as a $C_8$ splitter 157. The overhead stream from the $C_8$ splitter 157 contains a high proportion of ethylbenzene, together with some p- and m-xylenes. These leave the splitter through line 158 and are passed through a dehydrogenator 159, which converts the ethylbenzene to styrene. The dehydrogenated stream is fed through line 160 to another splitter 161, which is arranged to separate the $C_7$ and lighter materials, which leave through an overhead stream 162, from the heavier materials, which leave through bottoms line 163. These are small amounts of ethylbenzene and p- and m-xylene, and the sought for material styrene. The bottom stream leaving through line 163 is recycled to the feedstock stream passing through line 151.

The bottom stream from splitter 157 leaves through line 171. It is a stream of mixed xylenes, suitable for further processing.

The bottom stream leaving extractive distillation column 154 through line 164 is primarily styrene and solvent. These materials are passed through line 164 to solvent stripper 165, which separates the styrene from the solvent. The solvent leaves the stripper through line 155 and is recycled to the extractive distillation column 154. The styrene leaves the stripper 165 through overhead line 166, which passes it to a purification column 167. There, the styrene is separated as a purified product through side stream line 168, while the lighter impurities leave through overhead line 169 and the heavier impurities through bottoms line 170. These latter two streams may be recycled or discarded. The embodiment shown in FIG. 3 thus may be seen to share the advantage that ethylbenzene is thoroughly converted to styrene, thus increasing the recovery of styrene from the feedstock.

Figure 4:
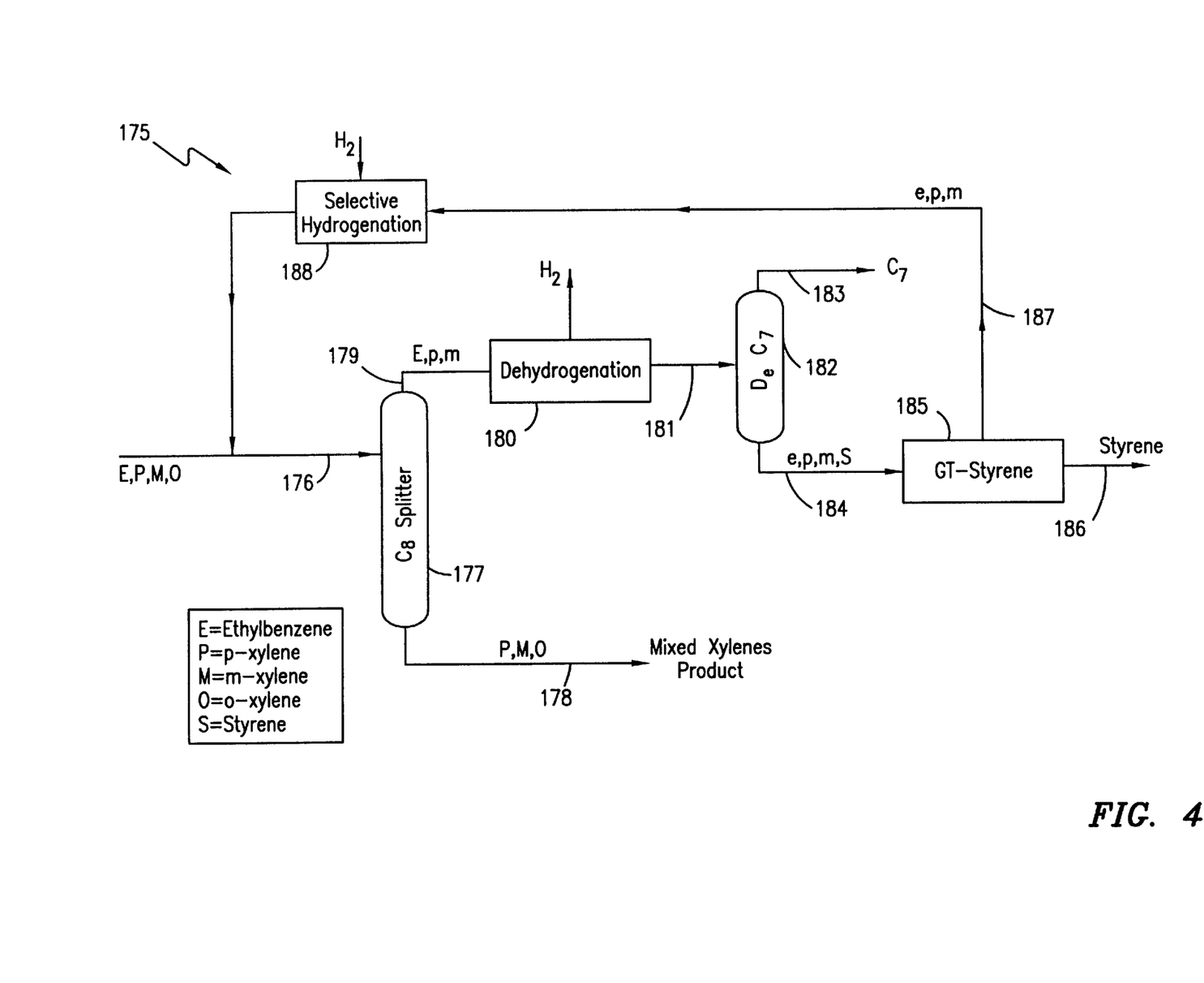
FIG. 4 is a diagrammatic illustration in elevation of an industrial plant for practicing still another preferred embodiment of the invention adapted especially for use with a feedstock having a $C_8$ reformate fraction with little or no initial styrene content.

The embodiment shown in FIG. 4 is a plant 175 arranged to produce styrene from a $C_8$ reformate fraction, which is a feedstock that ostensibly contains little or no styrene, being composed in the main of mixed xylenes and ethylbenzene. Substantial amounts of styrene are produced nonetheless from such a starting material in accordance with the invention. The feedstock enters the plant through line 176 and is fed first through column 177, which is operated as a $C_8$ splitter. The bottom stream out of the $C_8$ splitter through line 178 is a mixed xylenes stream, which is a product of value. The overhead stream leaving the $C_8$ splitter 177 through line 179 contains the bulk of the ethylbenzene, and small amounts of p- and m-xylene. This stream is dehydrogenated in dehydrogenator 180 to produce a stream containing styrene, which is fed through line 181 to another splitter arranged to separate $C_7$ and lighter materials from the balance of the feedstock. Splitter 182 thus produces an overhead stream through line 183 of $C_7$ and lighter materials. The main product stream out of splitter 182 through bottoms line 184 is a stream containing a minor amount of ethylbenzene, p- and m-xylene, and styrene. It thus resembles pyrolysis gasoline, and forms a suitable feedstock for the general process of the invention represented by block 185. Process block 185 should thus be understood to stand as a shorthand symbol for extractive distillation columns making use of an extractive distillation solvent which is preferably sulfolane and water, together with overhead and bottoms processing equipment of the kind disclosed and discussed in connection with FIG. 1 above. Thus, the ultimate product of such processing equipment represented by block 185 is a styrene stream through line 186, and a stream of mixed xylenes leaving through line 187. The mixed xylenes may be selectively hydrogenated in unit 188 and, in any event, are desirably recycled into the feedstock passing through 176. Block 188 converts any styrene that was not recovered in block 185 into ethylbenzene, so as not to contaminate the xylenes product in line 178 with unsaturated material. Block 188 may be located as shown, or after the feeds join in line 176, in which case it will totally saturate all components (except the aromatic ring itself) and eliminate the need for further treatment of the xylenes in line 178 to remove trace quantities of olefins originating from the reformate feedstock, which traces can cause an objectionable high acid-wash color in the xylenes product in line 178.

By the arrangement of FIG. 4, it is thus possible to obtain significant styrene production from $C_8$ reformate fractions from catalytic reformer plants, for example.

Figure 5:
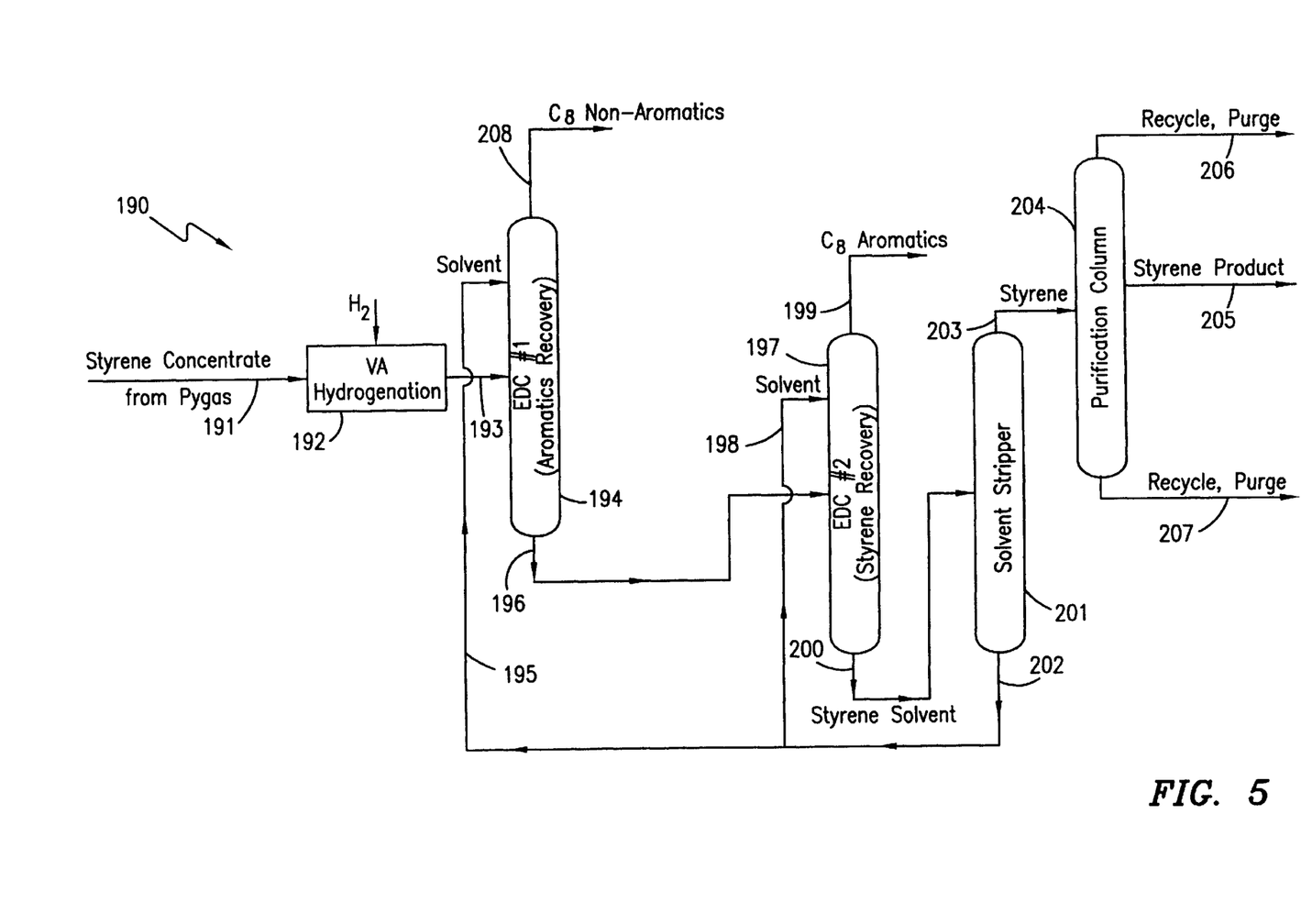
FIG. 5 is a diagrammatic illustration in elevation of an industrial plant for practicing still another preferred form of the invention involving especially separation of aromatic and non-aromatic $C_8$ streams in the course of the process.

The embodiment shown in FIG. 5 is a plant 190 in which an extractive distillation operation is employed to first separate $C_8$ non-aromatics from the balance of the feedstock, and then a further extractive distillation operation is conducted to separate and recover styrene from $C_8$ aromatics. Such an arrangement makes possible the production of $C_8$ aromatics which are suitable for xylene isomer production after hydro treatment to remove the trace unsaturated and sulphur compounds (such hydro treatment being not shown).

In the embodiment of FIG. 5, styrene containing pyrolysis gasoline feedstock is fed in through line 191. Again, it is mildly hydrogenated in vinyl acetylene hydrogenator 192 to remove acetylenic materials, and then fed through line 193 to an extractive distillation column 194 where it is extractively distilled with a solvent, preferably sulfolane and water fed in through line 195. The overhead stream out of extractive distillation column 194 is primarily non-aromatic $C_8$'s which leave through overhead line 208. The bottom stream is solvent, styrene, and aromatic $C_8$'s leaving through line 196, which feeds it to a second extractive distillation column 197, where it is extractively distilled with additional solvent fed in through line 198 to produce an overhead stream through line 199 of $C_8$ aromatics, which, as has been mentioned, form a suitable feedstock for xylene isomer production. The bottom stream out of extractive distillation column 197 leaving through line 200 is styrene and solvent. These two materials are separated in solvent stripper 201 to produce solvent as a bottom stream leaving through line 202, which splits into line 198 feeding column 197 and line 195 feeding column 194. The overhead stream out of solvent stripper 201 leaving through line 203 is styrene, which is separated in purification column 204. Purified styrene leaves as a side stream product through line 205, while light impurities leave as overhead through 206 and heavy impurities as a bottoms stream through line 207. The latter two streams may be recycled or purged.

Reasonable variations, modifications and adaptations for various usages and conditions can be made within the scope of the disclosure and the appended claims, without departing from the scope of the invention.

What is claimed is:

1. A process for recovering styrene from a feedstock containing at least styrene, ethylbenzene, xylenes, and one or more aromatic or non-aromatic hydrocarbon compounds comprising:

(a) separating said feedstock into a first stream relatively more concentrated in styrene than said feedstock and a second stream relatively more concentrated in ethylbenzene than said feedstock, said second stream being relatively high in xylenes content, by extractively distilling said feedstock in a single column utilizing a two-part extractive solvent consisting essentially of a first part selected from the group consisting of propylene carbonate, sulfolane (tetramethylene sulfone), methyl carbitol, 1-methyl-2-pyrrolidinone and mixtures thereof, but not including water, and a second part consisting of water, said two parts of said two-part extractive solvent being fed to said distillation column separately and independently at different locations along said single distillation column;

(b) recovering styrene from said first stream to produce a styrene product stream;

(c) dehydrogenating the ethylbenzene of said second stream without prior separation of xylenes from the ethylbenzene to produce additional styrene; and (d) recovering said additional styrene.

2. A process in accordance with claim 1 in which said additional styrene is recovered by recycling it into said feedstock.

3. A process for producing styrene from a feedstock containing styrene, ethylbenzene and at least one aromatic or non-aromatic hydrocarbon comprising:

feeding said feedstock into a single distillation column;

feeding a two-part extractive solvent into said distillation column, said solvent consisting essentially of a first part selected from the group consisting of propylene carbonate, sulfolane (tetramethylene sulfone), methyl carbitol, 1-methyl-2-pyrrolidinone, 2-pyrrolidinone and mixtures thereof, but not including water, and a second part consisting of water, said two parts of said two-part extractive solvent being fed to said distillation column separately and independently at different locations along said single distillation column;

distilling said feedstock in said distillation column in the presence of said extractive solvent to produce:

(a) a solvent fraction relatively rich in styrene compared to the feedstock fed to said distillation column; and (b) an overhead fraction comprising at least some of said at least one close boiling aromatic or non-aromatic hydrocarbon and being relatively lean in styrene compared to said feedstock;

withdrawing said solvent fraction from said distillation column;

withdrawing said overhead fraction from said distillation column; and separating at least styrene and ethylbenzene from one another in the course of performing the foregoing steps of said process;

in which said separation of styrene and ethylbenzene is effected in said distillation column; and in which ethylbenzene following its separation from styrene is dehydrogenated to produce additional styrene.

4. A process in accordance with claim 3 and further comprising hydrogenating at least part of said feedstock prior to feeding said feedstock to said distillation column to hydrogenate any acetylenic compounds therein under conditions avoiding conversion of substantial amounts of styrene to ethylbenzene.

5. A process in accordance with claim 4 in which said separated styrene is admixed with solvent after being withdrawn from said distillation column and further in which said separated styrene is thereafter separated from said admixed solvent.

6. A process in accordance with claim 4 in which said feedstock contains o-, p-, and m-xylenes and in which said feedstock, after said hydrogenation of at least part thereof, is separated to produce an overhead feedstock stream containing at least some ethylbenzene, some p-xylene, and some m-xylene, and a bottoms stream containing o-, p-, and m-xylenes, following which said overhead feedstock stream is dehydrogenated to produce some styrene therein, following which $C_7$'s and lighter components, if any, are separated therefrom prior to said hydrogenated feedstock being fed into said distillation column.

7. A process in accordance with claim 4 in which any non-aromatic components present in said hydrogenated feedstock are separated from said styrene in said distillation column.

8. A process in accordance with claim 7 in which said solvent fraction relatively rich in styrene is fed to a second distillation column, and additional extractive solvent is fed to said second distillation column, and further comprising distilling said styrene, said ethylbenzene and any other aromatic $C_8$ hydrocarbons present in said solvent fraction in the presence of said extractive solvent to effect a further separation of styrene from said ethylbenzene and said any other aromatic $C_8$ hydrocarbons, and withdrawing said separated styrene from said second distillation column.

9. A process in accordance with claim 3 in which said additional styrene is returned to said distillation column as a recycle stream.

10. A process in accordance with claim 3 in which said withdrawn solvent fraction containing styrene and at least some of said aromatic or non-aromatic hydrocarbon is fed to a second distillation column, additional extractive solvent is fed to said second distillation column, and further comprising distilling said styrene and said at least some of said at least one aromatic or non-aromatic hydrocarbon in the presence of said extractive solvent to effect a further separation of styrene from said at least some of said at least one aromatic or non-aromatic hydrocarbon; and withdrawing said further separated styrene from said second distillation column.

11. A process in accordance with claim 10 in which said further separated styrene is admixed with solvent after being withdrawn from said second distillation column and further in which said separated styrene is thereafter separated from said admixed solvent.

12. A process in accordance with claim 3 in which said feedstock contains xylenes and in which xylenes are partially removed from said separated ethylbenzene prior to said dehydrogenation.

13. A process for recovering styrene from a feedstock containing at least styrene, ethylbenzene, and o-xylene, m-xylene and p-xylene comprising:

hydrogenating said feedstock to hydrogenate any acetylenic compounds therein, while avoiding conversion of substantial amounts of styrene to ethylbenzene;

feeding said hydrogenated feedstock into first distillation column;

feeding a two-part extractive solvent into said first distillation column, said solvent consisting essentially of a first part selected from the group consisting of propylene carbonate, sulfolane (tetramethylene sulfone), methyl carbitol, 1-methyl-2-pyrrolidinone and mixtures thereof, but not including water, and a second part consisting of water, said two parts of said two-part extractive solvent being fed to said distillation column separately and independently at different locations along said first distillation column;

distilling said feedstock in said first distillation column in the presence of said extractive solvent to produce:

(a) a first solvent fraction containing styrene, o-xylene, m-xylene, p-xylene and said extractive solvent; and
(b) a first overhead fraction containing ethylbenzene, p-xylene and m-xylene; dehydrogenating said first overhead fraction without prior separation of xylenes therein to produce additional styrene;

feeding said dehydrogenated first overhead fraction to a second distillation column and distilling it there to produce:
(c) a second overhead fraction containing $C_7$ and lighter hydrocarbon materials; and
(d) a bottoms stream containing styrene, ethylbenzene, p-xylene and m-xylene;

recycling said bottoms stream to said hydrogenation step;
withdrawing said second overhead fraction;
feeding said first solvent fraction to a third distillation column;
feeding said two-part extractive distillation solvent into said third distillation column;
distilling said first solvent fraction in said third distillation column in the presence of said extractive solvent to produce:
(e) a second solvent fraction containing said solvent and styrene; and
(f) a third overhead fraction containing mixed xylenes;
stripping and withdrawing styrene from said extractive solvent in said second solvent fraction; and
recycling said stripped extractive solvent to said first and third distillation columns for use therein.

14. A process in accordance with claim 13 comprising purifying said withdrawn styrene by distilling it in a column and withdrawing purified styrene as a side stream.

15. A process for recovering styrene from a feedstock containing at least styrene, ethylbenzene, o-xylene and p-xylene comprising:
hydrogenating said feedstock to hydrogenate any acetylenic compounds therein while avoiding conversion of substantial amounts of styrene to ethylbenzene;
feeding said hydrogenated feedstock into a first distillation column;
feeding a two-part extractive solvent into said first distillation column, said solvent consisting essentially of a first part select from the group consisting of propylene carbonates, sulfolane, methyl carbitol, 1-methyl-2-pyrrolidinone, 2-pyrrolidinone, and mixtures thereof, but not including water, and a second part consisting of water, said two parts of said two-part extractive solvent being fed to said distillation column separately and independently at different locations along said third distillation column;
distilling said feedstock in said first distillation column in the presence of said extractive solvent to produce:
(a) a first solvent fraction containing styrene and said extractive solvent; and
(b) a first overhead fraction containing ethylbenzene, o-xylene, m-xylene, and p-xylene;
feeding said first overhead fraction to a second distillation column and distilling it there to produce:
(c) a bottoms fraction containing mixed xylenes; and
(d) a second overhead fraction containing ethylbenzene, p-xylene, and m-xylene;
dehydrogenating said second overhead fraction without prior separation of xylenes therein to produce additional styrene;
feeding said dehydrogenated second overhead fraction to a third distillation column and distilling it there to produce:
(e) a third overhead fraction containing $C_7$ and lighter hydrocarbon materials; and
(f) a second bottoms fraction containing styrene, ethylbenzene p-xylene and m-xylene;
withdrawing said third overhead fraction;
recycling said second bottoms fraction into said feedstock;
stripping and withdrawing styrene from extractive solvent in said first solvent fraction; and
recycling said stripped extractive solvent to said first distillation column for use therein.

16. A process in accordance with claim 15 comprising purifying said withdrawn styrene by distilling it in a column and withdrawing purified styrene as a side stream.

17. A process for producing styrene from a $C_8$ reformate fraction feedstock containing ethylbenzene, o-xylene, m-xylene and p-xylene and substantially no styrene comprising:
splitting said $C_8$ reformate fraction feedstock in a first distillation column to produce first overhead stream containing ethylbenzene and a portion of the m-xylene and p-xylene in said feedstock and a first bottom stream containing o-xylene, m-xylene and p-xylene;
dehydrogenating said first overhead stream to convert at least part of the ethylbenzene therein to styrene;
splitting said dehydrogenated first overhead stream in a second distillation column to produce a second overhead stream containing $C_8$ and lighter hydrocarbons and a second bottom stream containing styrene, ethylbenzene, p-xylene and m-xylene;
feeding said second bottom stream into a third distillation column;
feeding a two-part extractive distillation solvent into said third distillation column, said solvent consisting essentially of a first part selected from the group consisting of propylene carbonate, sulfolane (tetramethylene sulfone), methyl carbitol, 1-methyl-2-pyrrolidinone, 2-pyrrolidinone and mixtures thereof, but not including water, and a second part consisting of water, said two parts of said two-part extractive solvent being fed to said distillation column separately and independently at different locations along said third distillation column;
distilling said second bottom stream in said third distillation column in the presence of said extractive distillation solvent to produce:
(a) a solvent fraction containing styrene and solvent; and
(b) a third overhead stream containing ethylbenzene, p-xylene, and m-xylene; recycling said third overhead stream to said $C_8$ reformate fraction feedstock; stripping and removing styrene from solvent in said solvent fraction; and recycling said stripped solvent to said third distillation column.

18. A process in accordance with claim 17 and further comprising hydrogenating said third overhead stream to convert any unrecovered styrene to ethylbenzene.

19. A process for recovering styrene from a feedstock containing at least styrene, ethylbenzene, o-xylene, m-xylene, p-xylene, and/or other close-boiling non-aromatic hydrocarbons comprising:
hydrogenating said feedstock to hydrogenate any acetylenic compounds therein while avoiding conversion of substantial amounts of styrene to ethylbenzene;
feeding said hydrogenated feedstock into a first distillation column;

feeding a two-part extractive solvent into said first distillation column, said solvent consisting essentially of a first part selected from the group consisting of propylene carbonate, sulfolane (tetramethylene sulfone), methyl carbitol, 1-methyl-2-pyrrolidinone and 2-pyrrolidinone, and mixtures thereof, but not including water, and a second part consisting of water, said two parts of said two-part extractive solvent being fed to said distillation column separately and independently at different locations along said first distillation column;

distilling said feedstock in said first distillation column in the presence of said extractive solvent to produce:
(a) a first solvent fraction containing styrene, o-xylene, m-xylene, p-xylene and said extractive solvent; and
(b) a first overhead fraction containing $C_8$ non-aromatics; feeding said first solvent fraction to a second distillation column; feeding said two-part extractive distillation solvent into said second distillation column;

distilling said first solvent fraction in said second distillation column in the presence of said extractive solvent to produce:
(c) a second solvent fraction containing said solvent and styrene; and
(d) a second overhead fraction containing $C_8$ aromatics;

stripping and withdrawing styrene from said extractive solvent in said second solvent fraction; and recycling said stripped extractive solvent to said first and second distillation columns for use therein.

20. A process in accordance with claim 19 comprising purifying said withdrawn styrene by distilling it in a column and withdrawing purified styrene as a side stream.

* * * * *

UNITED STATES PATENT AND TRADEMARK OFFICE
CERTIFICATE OF CORRECTION

PATENT NO. : 5,877,385
DATED : March 2, 1999
INVENTOR(S) : Fu-Ming Lee et al.

It is certified that error appears in the above-indentified patent and that said Letters Patent is hereby corrected as shown below:

Column 4, line 19    Delete "1-methyl-2-pyrrolidone"    Insert --1-methyl-2-pyrrolidinone--

Signed and Sealed this

Twenty-seventh Day of July, 1999

Attest:

Attesting Officer

Q. TODD DICKINSON

Acting Commissioner of Patents and Trademarks